US009518336B2

(12) United States Patent
Markham et al.

(10) Patent No.: US 9,518,336 B2
(45) Date of Patent: Dec. 13, 2016

(54) SYNTHETIC DIAMOND MATERIALS FOR QUANTUM AND OPTICAL APPLICATIONS AND METHODS OF MAKING THE SAME

(71) Applicants: ELEMENT SIX LIMITED, Ballasalla (IM); PRESIDENT AND FELLOWS OF HARVARD COLLEGE, Cambridge, MA (US)

(72) Inventors: Matthew Markham, Oxfordshire (GB); Alastair Stacey, Oxfordshire (GB); Nathalie De Leon, Cambridge, MA (US); Yiwen Chu, Cambridge, MA (US); Brendan John Shields, Cambridge, MA (US); Birgit Judith Maria Hausmann, Cambridge, MA (US); Patrick Maletinsky, Cambridge, MA (US); Ruffin Eley Evans, Cambridge, MA (US); Amir Yacoby, Cambridge, MA (US); Hongkun Park, Cambridge, MA (US); Marko Loncar, Cambridge, MA (US); Mikhail D. Lukin, Cambridge, MA (US)

(73) Assignees: Element Six Limited (IM); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/646,384

(22) PCT Filed: Dec. 4, 2013

(86) PCT No.: PCT/EP2013/075563
§ 371 (c)(1),
(2) Date: May 20, 2015

(87) PCT Pub. No.: WO2014/090662
PCT Pub. Date: Jun. 19, 2014

(65) Prior Publication Data
US 2015/0299894 A1   Oct. 22, 2015

Related U.S. Application Data

(66) Substitute for application No. 61/737,001, filed on Dec. 13, 2012.

(30) Foreign Application Priority Data

Jan. 29, 2013   (GB) .................................. 1301556.5

(51) Int. Cl.
*C01B 31/06* (2006.01)
*C30B 1/04* (2006.01)
(Continued)

(52) U.S. Cl.
CPC .................. *C30B 1/04* (2013.01); *B82Y 10/00* (2013.01); *C30B 29/04* (2013.01); *C30B 30/00* (2013.01);
(Continued)

(58) Field of Classification Search
CPC ................................ C30B 29/04; C01B 31/06
(Continued)

(56) References Cited

U.S. PATENT DOCUMENTS

2011/0163291 A1 * 7/2011 Scarsbrook .......... G06N 99/002 257/9
2011/0309265 A1   12/2011 Babinec et al.

FOREIGN PATENT DOCUMENTS

JP    2008526682 A    7/2008
JP    2012530674 A    6/2012
(Continued)

OTHER PUBLICATIONS

University of Helsinki, "Confocal Microscopy Tutorial" [online], Mar. 23, 2004, retrieved http://www.hi.helsinki.fi/amu/AMU %20Cf_tut/Opt_average.htm on Apr. 1, 2016.*
(Continued)

*Primary Examiner* — David Porta
*Assistant Examiner* — Abra Fein
(74) *Attorney, Agent, or Firm* — Armstrong Teasdale LLP (57) ABSTRACT

A synthetic diamond material comprising one or more spin defects having a full width half maximum intrinsic inhomogeneous zero phonon line width of no more than 100 MHz. The method for obtain such a material involves a multi-stage annealing process.

15 Claims, 4 Drawing Sheets

(51) Int. Cl.
| | |
|---|---|
| C30B 29/04 | (2006.01) |
| C30B 33/02 | (2006.01) |
| G06N 99/00 | (2010.01) |
| B82Y 10/00 | (2011.01) |
| C30B 30/00 | (2006.01) |
| G01N 21/64 | (2006.01) |

(52) U.S. Cl.
CPC .............. *C30B 33/02* (2013.01); *G01N 21/64* (2013.01); *G06N 99/002* (2013.01); *G01N 2021/6497* (2013.01)

(58) Field of Classification Search
USPC ........................................ 250/458.1; 423/446
See application file for complete search history.

(56) References Cited

FOREIGN PATENT DOCUMENTS

| | | |
|---|---|---|
| JP | 2012530677 A | 6/2012 |
| WO | 01/96633 A1 | 12/2001 |
| WO | 2006076354 A2 | 7/2006 |
| WO | 2010/010344 A1 | 1/2010 |
| WO | 2010/010352 A1 | 1/2010 |
| WO | 2010149775 A1 | 12/2010 |
| WO | 2010149779 A1 | 12/2010 |

OTHER PUBLICATIONS

International Search Report for PCT/EP2013/075563 dated Jan. 17, 2014.
UKIPO Search Report for GB1301556.5 dated Jul. 16, 2013.
UKIPO Search Report for GB1321381.4 dated May 19, 2014.
Yumin et al; Zero-phonon linewidth of single nitrogen vacancy centers in diamond nanocrystals; Jan. 11, 2008; p. 033201; vol. 77; Physical Review B, Oregon, US.
Waldermann et al; Creating diamond color centers for quantum optical applications; Sep. 3, 2007; pp. 1889-1890; vol. 16 No. 11; Elsevier Science Publishers,Diamond and Related Materials, Amsterdam, NL.
Bernien et al; Two-photon quantum interference from separate nitrogen vacancy centers in Diamond; Jan. 27, 2012; p. 043604; vol. 108 No. 4; Physical Review Letters, American Physical Society, US.
Acosta et al; Dynamic Stabilization of the Optical Resonances of Single Nitrogen-vacancy centers in diamond; May 12, 2012; p. 206401; vol. 108; Physical Review Letters, American Physical Society, US.
Fish et al; Photoluminescence spectroscopy of synthetic diamond; 1997; p. 103-105; vol. 239-241; Materials Science Forum, Trans Tech Publications, CH.
Faraon et al; Coupling of Nitrogen-Vacancy Centers to Photonic Crystal Cavities in Monocrystalline Diamond; Jul. 19, 2012; p. 033604; vol. 109; Physical Review Letters, American Physical Society, US.
Okamato et al; Near-field scanning optical microscopy of photonic crystal nanocavities; Mar. 17, 2003; p. 1676; vol. 82; Applied Physics Letters, American Institute of Physics, US.
McDaniel et al; Local characterization of transmission properties of a two-dimensional photonic crystal; Apr. 15, 1997; p. 10878-10882; vol. 55; Physical Review B, American Physical Society, US.
Rabeau et al; Implantation of Labelled Single Nitrogen Vacancy Centers in Diamond Using 15N; 2006; p. 023113; vol. 88; Applied Physics Letters, American Institute of Physics, US.
Fu et al; Conversion of neutral nitrogen-vacancy centers to negatively charged nitrogen-vacancy centers through selective oxidation; Mar. 23, 2006; p. 121907; vol. 96; Applied Physics Letters, American Institute of Physics, US.
Lettow et al; Quantum Interference of Tunably Indistinguishable Photons from Remote Organic Molecules; Mar. 26, 2010; p. 123605; vol. 104; Physical Review Letters, American Physical Society, US.
Patel et al; Tow-Proton Interference of the Emission from Electrically Tunable Remote Quantum Dots; Jul. 11, 2010; p. 632-635; vol. 4; Nature Photonics, Macmillan Publishers Limited, US.
Flagg et al; Interference of Single Photons from Two Separate Semiconductor Quantum Dots; Apr. 1, 2010; p. 137401; vol. 104; Physical Review Letters, American Physical Society, US.
Tamarat et al; Stark shift control of single optical centers in diamond; Aug. 23, 2006; p. 083002; vol. 97; Physical Review Letters, American Physical Society, US.
Bassett et al; Electrical Tuning of Single Nitrogen-Vacancy Center Optical Transitions Enhanced by Photoinduced Fields; Dec. 22, 2011; p. 266403; vol. 107; Physical Review Letters, American Physical Society, US.
Sanaka et al; Indistinguishable Photons from Independent Semiconductor Nanostructures; Jul. 31, 2009; p. 053601; vol. 103; Physical Review Letters, American Physical Society, US.
Shen et al; Zero-phonon linewidth of single nitrogen vacancy centers in diamond nanocrystals; Jan. 11, 2008; p. 033201; vol. 77; Physical Review B, American Physical Society, US.
Santori et al; Vertical distribution of nitrogen-vacancy centers in diamond formed by ion implantation and annealing;Mar. 16, 2009; p. 125313; vol. 79; Physical Review B, American Physical Society, US.
Kai-Mei Fu et al., "Observation of the Dynamic Jahn-Teller Effect in the Excited States of Nitrogen-Vacancy Centers in Diamond", Physical Review Letters, American Physical Society, Dec. 18, 2009, vol. 103, pp. 256404-1-256404-4.

\* cited by examiner

SYNTHETIC DIAMOND MATERIALS FOR QUANTUM AND OPTICAL APPLICATIONS AND METHODS OF MAKING THE SAME

This application is the national stage entry under 371(c) of PCT/EP2013/075563 filed on Dec. 4, 2013 which claims priority to U.S. Provisional Application No. 61/737,001 filed on Dec. 13, 2012.

FIELD OF INVENTION

The present invention relates to synthetic diamond materials for quantum and optical applications (e.g. quantum optics, quantum information processing, quantum key distribution, single photon sources, quantum repeaters, and/or quantum based sensing devices such as magnetometers) and methods of making the same. Certain embodiments relate to methods of synthesising and subsequently treating diamond materials in order to provide improved emission characteristics from spin defects disposed within the synthetic diamond materials. Particular embodiments relate to chemical vapour deposited (CVD) diamond materials.

BACKGROUND OF INVENTION

Quantum emitters (including alkali atoms, trapped ions, solid state defects, and quantum dots) strongly coupled to photons have a wide range of technological applications in photonic computing, quantum information processing, quantum sensing and metrology, and quantum networks. The requirements for most of these applications are that photons interact with the emitter with high probability (the emitter has a large absorption cross section), and are collected with high probability. One major prerequisite to fulfil these requirements is that the emission be Fourier transform-limited, i.e. that the line width of the emission be determined only by the lifetime of the excited state. When the line width is broader than this transform-limited line width, additional de-phasing leads to a decrease in the absorption cross-section and a decrease in the effective collection efficiency. A broader line width can be due to coupling to phonons, spectral diffusion, or other non-radiative decay channels.

A quantum emitter with a transform-limited line width that is well localized to a single layer in a solid-state material can be used to construct devices that enable strong single-photon nonlinearities. By coupling a quantum emitter to a single mode waveguide, for example, one can realize a single photon transistor, in which the propagation of one photon is controlled by the internal state of the emitter, which is in turn manipulated by another photon. Such a device is a key building block for photonic computing platforms.

Furthermore, quantum emitters such as a nitrogen-vacancy (NV) center in diamond can be used as nanoscale magnetometers, and increasing the photon collection efficiency can improve the sensitivity drastically. An NV center with a transform-limited zero phonon line (ZPL) can be used to detect external spins with high sensitivity. For this application, it is also important that the NV be localized close to the diamond surface, since magnetic fields from external sources decay rapidly with distance.

Additionally, NV centers with transform-limited line widths can be employed in hybrid quantum systems, in which the NV center is coupled to another quantum system such as a superconducting circuit for microwave to photon conversion, optomechanical systems for photon-phonon conversion, and optoelectronic devices.

Multi-photon quantum entanglement from multiple photon emitters is considered to be a key ingredient for certain quantum processing applications. To achieve such entanglement requires the photons from different emitters to be quantum mechanically indistinguishable.

Multi-photon quantum entanglement from multiple gas state emitters, including emission from a single atom/ion in a trap, is known. This is achieved by generating photon emission from gas state emitters which is identical in terms of bandwidth, frequency, and polarization such that photons from different emitters are quantum mechanically indistinguishable. These identical photons can then be overlapped in a beamsplitter to achieve remote quantum entanglement.

The aforementioned approach is problematic for solid state emitters. This is because the energies of optical transitions in solid state systems vary due to variations in the electronic environment and strain within solid state crystal systems. Differences in emission characteristics of solid state emitters may be caused by impurities, intrinsic crystal defects such as dislocations, extrinsic defects such as those resulting from processing damage, and/or other extrinsic effects such as Stark tuning by electric field. As such, photons emitted from two different solid state emitters vary in terms of bandwidth, frequency, and polarization and are quantum mechanically distinguishable. Accordingly, such photons do not undergo quantum entanglement when overlapped on a beamsplitter or comparable arrangement.

One solution to the aforementioned problem is to reduce the resolution of a detector arrangement used to detect photons from photon emitters to an extent that the photons from different sources are indistinguishable to the detectors. For example, by using detectors with a high time resolution this in turn leads to a low frequency resolution, which can render the photons indistinguishable. However, the higher timing resolution requires that the count rates in each bin be higher than noise, such as dark counts, and single photon emission from defects in solid state materials can be very weak. For example, the photon emissive nitrogen-vacancy defect ($NV^-$) in diamond material, which is a leading candidate for solid state quantum processing applications, exhibits a broad spectral emission associated with a Debye-Waller factor of the order of 0.05, even at low temperature. Emission of single photons in the Zero-Phonon Line (ZPL) is then typically of the order of a hundred thousand of photons per second. Due to poor collection efficiency only approximately 0.1-1% of this emission is typically detected resulting in low count rates. Such count rates are insufficient for the realization of advanced quantum information processing protocols within reasonable data acquisition times based on photon interference using high time resolution. (i.e. low frequency resolution) detectors.

In fact, the aforementioned issues are so problematic that multi-photon quantum interference from multiple solid state quantum registers had not been demonstrated in practice until 2011 (Phys. Rev. Lett. 108, 043604 (2012). In this regard, it should be noted that a solid state quantum register can comprise both nuclear and electron spins coupled together. An electron spin can function as a control qubit with optical spin state detection and fast high fidelity coherent manipulation. A nuclear spin can function as a memory qubit which has weak interaction with the surrounding environment. Together, an electron spin and a nuclear spin coupled can form a quantum register. An example of such a quantum register is a nitrogen-vacancy defect in diamond material which has resolvable electron spin states that are optically addressable and coupled to nuclear spin states of the nitrogen nucleus and/or $^{13}C$ nuclei in the surrounding diamond lattice. It should be noted that a quantum register of this kind differs from systems which only comprise single spin emitters, decoupled spin states, or emitters which do not comprise spin states which can be resolved to function as a quantum register.

In relation to the above, it is noted that multi-photon interference has been observed from more simple solid state systems such as quantum dots, single molecules adsorbed onto a surface, and F-dopants in ZnSe [see, for example, R. Lettow et al., Physical Review Letters 104 (2010); Patel et al., Nature Photonics 2010, DOI: 10.1038/NPHOTON.2010.161; Sanaka et al., PRL 103, 053601 (2009); and Flagg et al., Phys. Rev. Lett. 104, 137401 (2010)]. However, multi-photon quantum interference from multiple spin resolved solid state quantum registers has not been demonstrated in practice to date due to the previously described problems. Quantum dots in III-V semiconductors relate to electronic transitions in a dense nuclear spin bath and thus are unsuitable for quantum information processing applications requiring a nuclear spin memory qubit. Single molecules adsorbed onto a surface do not exhibit spin resolved emission suitable for information processing. Furthermore, surface crystallized single molecule systems are inherently fragile systems which may be unsuitable for commercial device applications. F-dopants in ZnSe have not been demonstrated to comprise spin resolved solid state quantum registers in which resolvable electron spin states are coupled to one or more nuclear spins.

In contrast to the above, in 2011 multi-photon quantum interference from multiple spin resolved solid state quantum registers was demonstrated for $NV^-$ spin defects in CVD synthetic diamond material. This was achieved by providing a combination of features including:

(i) Synthesis of very high purity, low strain CVD synthetic diamond material comprising $NV^-$ spin defects in a relatively uniform electronic and strain environment;

(ii) Selection of two $NV^-$ spin defects with nearly identical frequency within the high purity, low strain CVD synthetic diamond material;

(iii) Fabrication of solid immersion lenses in the high purity, low strain CVD synthetic diamond material over each of the selected $NV^-$ spin defects to increase optical out-coupling of photons emitted by the $NV^-$ spin defects;

(iv) Stark tuning of the $NV^-$ defects to reduce the difference in frequency between the two $NV^-$ spin defects;

(v) Filtering of the photons emitted by the two selected $NV^-$ defects using a dichroic mirror configured to separate a zero phonon $NV^-$ line emission from a phonon side band emission;

(vi) Further filtering of the emitted photons using a polarizing beam splitter;

(vii) Overlapping the filtered photons from each $NV^-$ spin defect on a fibre beam splitter; and (viii) Detecting the tuned and filtered photon emission using a detector arrangement which is configured to resolve sufficiently small differences in photon detection times that the tuned and filtered photon emission from the $NV^-$ spin defects is quantum mechanically indistinguishable resulting in quantum interference between indistinguishable photon emission from the two $NV^-$ spin defects.

The aforementioned approach has proved successful in demonstrating an approach to achieve multi-photon interference from solid-state emitters which may be used in quantum processing applications. However, the tuned and filtered photon emission is still relatively weak with a relatively low proportion of the emitted photons being detected resulting in low photon count rates and relatively long data acquisition times. For commercial devices it would be desirable to further increase the photon count rates and reduce data acquisition times.

Accordingly, there is still a need to provide a device which is capable of providing multi-photon quantum interference from multiple solid state quantum registers at faster data acquisition times.

In this regard, the inhomogeneous broadening and spectral variation relative to the natural emission line width of each solid state photon emitter will limit the observability of quantum interference as emitted photons will be spread over a range of frequencies such that a significant proportion of photons will be quantum mechanically distinguishable. Tuning and filtering the emission can be used in combination with a suitably configured detector to observe quantum interference as previously described but a significant proportion of photons are discarded in such an approach leading to relatively low photon count rates and relatively long data acquisition times. As such, it would be desirable to provide a synthetic diamond material which comprises spin defects having a narrower emission line width in order to reduce or eliminate the need for tuning and filtering of the emission to achieve multi-photon interference at higher photon count rates and reduced data acquisition times.

Fluorescence from the NV can be separated into two components with a standard branching ratio between them: the zero phonon line (ZPL) and the phonon side band (PSB). Typical branching ratios, as measured, are 1:20 or 1:30. The PSB is broad, spanning more than 100 nm, and results from vibronic transitions that cannot be frozen out (e.g., their intensity is determined by Franck-Condon factors between the excited state and various phonon excited, electron ground states, and the Debye-Waller factor is 0.03-0.05). The theoretical minimum line width of a solid state emitter is known as the (Fourier) transform-limited line width and is determined by the excited state lifetime of the emitter. For $NV^-$, this is phonon broadened at room temperature to about 1 THz (Phys. Rev. Lett., vol. 103, issue 25, pp 256404, 2009) but below approximately 10 K, the line width can in principle be transform-limited. The excited state lifetime of the NV center has been measured to be 12 ns ($\tau$), which is what limits the natural line width to $\delta\upsilon=(1/2\pi\tau)=13$ MHz in an ideal material. In almost all diamond materials (natural, CVD synthetic, high pressure high temperature (HPHT) synthetic, and nanodiamond) the line width is significantly larger than this fundamental limit and each defect shows variation. This is due to the fact that each defect has a different local electronic and strain environment. For example, it has been noted that even though the multi-photon interference configuration previously described utilized a CVD synthetic diamond material with very high purity and low strain to provide $NV^-$ spin defects in a relatively uniform electronic and strain environment, the emission line width for each $NV^-$ spin defect was still significantly higher than the theoretical limit of 13 MHz. Individual photoluminescent excitation spectra (single-scans), recorded in the absence of green light, showed a zero phonon line width of 36 MHz and 38 MHz for the two selected $NV^-$ spin defects with a 532 nm repump pulse between scans leading to an overall total distribution of frequencies with a line width of a few hundred MHz. Spectral diffusion was also observed in photoluminescent excitation spectra recorded with simultaneous green excitation and in the zero phonon line emission spectrum under 532 nm excitation. Emission line broadening over time is known in the art as inhomogeneous line broadening and the overall total spectral line width measured over time is known as the inhomogeneous line width. This contrasts with a line width measured at a specific instance in time known as the single scan line width. However, despite the observed inhomogeneous broadening exceeding the radiative line width by an order of magnitude, two photon interference effects were still detected due to the application of suitable tuning and filtering and a detector configured such that the zero phonon emission line width did not exceed the inverse time resolution of the photon detectors.

The table below gives some examples of zero phonon line widths measured in different types of diamond materials.

| Type | Sample | $NV^-$ zero phonon linewidth |
| --- | --- | --- |
| $NV^-$ spin defects in natural diamond materials | "Type IIa" crystal | ~50 MHz |
| Naturally occurring $NV^-$ spin defects in synthetic diamond materials | A type IIa nanocrystal (Shen, PRB 2008) | 16 MHz (single scan, not including spectral diffusion) |
|  | Electronic grade CVD | ~30 MHz to ~500 MHz (single scan, not including spectral diffusion) |
|  | Nanobeams in type IIa | ~10 s of GHz |
| $NV^-$ spin defects introduced into electronic grade CVD diamond | Implantation, bulk | ~100 MHz to few GHz (single scan, not including spectral diffusion) |
|  | Electron irradiation, bulk | ~30 MHz to 100 MHz (single scan, not including spectral diffusion) |

Natural diamond materials have a large variety of $NV^-$ zero phonon line widths reflecting the large variety of diamond crystal structures found in nature. While every diamond crystal is unique, high purity type IIa natural diamonds can have a zero phonon line width of the order to 50 MHz. In one famous natural diamond from the Urals a stable zero phonon line width of less than 20 MHz has been observed. For example, P. Tamarat et al. [Phys. Rev. Lett. 97, 083002 (2006)] have studied this unique natural diamond and reported an $NV^-$ zero phonon line which is at the transform limited line width of 13 MHz and which is stable over many seconds and excitation cycles. However, the reasons why $NV^-$ spin defects exhibit such narrow and stable emission characteristics in this single natural diamond sample are not currently well understood. Furthermore, such narrow, stable zero phonon line widths have not been observed to date in any synthetic diamond materials.

Synthetic diamond materials also have a large variety of $NV^-$ zero phonon line widths reflecting the large variety of synthesis techniques and recipes for targeting different diamond materials having properties optimized for particular applications. Synthetic diamond materials can be distinguished from natural diamond materials using a range of spectroscopic techniques known in the art because synthetic materials have a different composition of extended defects (e.g. dislocations) and impurity defects when compared with natural diamond materials. Synthetic diamond materials are advantageous over natural materials for technical applications in that the use of a specific synthesis technique and recipe can lead to a reproducible product material.

Despite the above, at the date of writing this specification the present inventors are not aware of any disclosure of a route to achieving synthetic diamond material with a stable inhomogeneous spin defect zero phonon line width of less than 100 MHz. Where line width values below 100 MHz have been reported, these are measured over a single scan and do not include spectral diffusion.

An $NV^-$ zero phonon line width of 16 MHz has been reported by Shen et al. [Phys. Rev. B 77, 033201 (2008)] in a synthetic type IIa nanodiamond. However, this line width was measured from an individual photoluminescent excitation spectrum and is subject to spectral diffusion leading to line broadening over time. That is, the emission line frequency moves over time such that while at a single instance the line width may be narrow, when the line width is measured over a number of spectral scans summed together the overall distribution of frequencies results in an inhomogeneous line width greater than 100 MHz.

V. M. Acosta et al. [Phys. Rev. Lett. 108, 206401 (2012)] have recently reported the application of a dynamic feedback Stark tuning technique for reducing spectral diffusion of $NV^-$ emission frequency over time leading to spectral broadening. An average single scan line width of 140 MHz is reported for an $NV^-$ defect located in a 100 nm thick CVD synthetic diamond film deposited on a high purity 100-oriented diamond substrate. A much narrower $NV^-$ line width of 60 MHz is reported for a natural type IIa diamond sample. It is reported that spectral diffusion of a zero phonon emission line in the natural sample was supressed to 16 MHz standard deviation by application of the dynamic feedback Stark tuning technique. However, the 16 MHz figure represents the spectral drift from the starting line position and not the single scan line width which was unchanged by the dynamic feedback Stark tuning technique and remained at 60 MHz. In any case, the 60 MHz value is for the natural diamond sample rather than the synthetic diamond sample.

Other background references include the following:
Faraon et al. PRL 109, 033604 (2012) [http://prl.aps.org/pdf/PRL/v109/i3/e033604] discloses NV spin defects in a type IIa photonic device with a 4 GHz line width;
Kai-Mei C. Fu, PRL 103, 256404 (2009) [http://prl.aps.org/pdf/PRL/v103/i25/e256404] discloses NV defects in electronic grade material with an ~30 MHz single scan line width; and
Bernien PRL 108, 043604 (2012) [http://prl.aps.org/pdf/PRL/v108/i4/e043604] discloses NV spin defects in electronic grade material with a 263 MHz inhomogeneous line width and 36 MHz single scan line width.

It should be noted that in the previous discussion references to the zero phonon line width of a spin defect have been in relation to the intrinsic line width of the emission with no photonic cavity broadening. In certain quantum or optical applications it is advantageous to couple one or more spin defects to an optical cavity or photonic cavity structure. Such a photonic cavity can be used to increase the number of photons emitted in the zero phonon line and also increases the width of the zero phonon line via cavity broadening, as a function of the Q-factor of the cavity. As such, in quantum device structures which utilize a photonic cavity the observed zero phonon line width will be larger than the intrinsic line width of the spin defect if no photonic cavity was present. It should be noted that even when a photonic cavity structure is provided it is still advantageous to provide a spin defect which has an intrinsically narrow zero phonon line width emission. The term intrinsic inhomogeneous zero phonon line width will be used herein to relate to the intrinsic inhomogeneous zero phonon line width of the spin defect with no photonic cavity broadening and with no Stark tuning to counteract spectral drift. If a photonic cavity is present, then the effect of cavity broadening can be subtracted from the observed zero phonon line width to determine the intrinsic inhomogeneous zero phonon line width of the spin defect. In order to extract the intrinsic line width of an NV center that is radiatively broadened by the presence of a cavity, time-dependent fluorescence measurements can be used to extract the lifetime of the NV center. This line width, measured by resonant absorption/fluorescence, is simply the inverse of the measured lifetime $\delta\upsilon=(1/2\pi\tau)$ which will be a combination of the cavity broadening and the intrinsic line width. The maximum amount that the line width can decrease is given by the Purcell factor, assuming optimal NV alignment within the cavity. The Purcell factor can be calculated from the cavity Q and the mode volume. The cavity Q and resonance position can be characterized independently by a variety of techniques, such as transmission, tapered fiber coupling, and cross-polarized scattering. The mode volume is harder to characterize externally (typically being calculated or simulated) but can be done using near-field scanning techniques [Okamato et al, Appl. Phys. Lett. 82, 1676 (2003) and McDaniel et al, Phys. Rev. B 55, 10878-10882 (1997)]. Another approach to measure the actual contribution of the cavity to the NV line width is to tune the NV center and cavity out of resonance with one another. Typical achievable NV detunings by the Stark effect and micro-fabricated electrodes are of the order of 100 GHz [Phys. Rev. Lett., vol. 97, issue 8, pp 083002, 2006 and Phys. Rev. Lett., vol. 107, issue 26, pp. 266403, 2011]. This is feasible for cavities with Q>5000. It is also possible to tune the cavity by condensation of noble gases, deposition of other dielectrics, and etching. When the cavity and NV are detuned, the lifetime of the NV center should increase to its natural lifetime, and its line width should reflect the intrinsic line width of the NV without the cavity.

In addition to the above, it should also be noted that the method of measuring the zero phonon line width can affect the observed zero phonon line width. For example, measuring the zero phonon line width at temperatures significantly above the Debye Temperature leads to temperature induced phonon broadening. Furthermore, exciting the spin defect at high laser powers can lead to power broadening of the zero phonon line emission. Accordingly, in addition to the above, the term intrinsic inhomogeneous zero phonon line width will be used herein to relate to the inhomogeneous zero phonon line width which is measured at a sample temperature low enough to inhibit phonon broadening, and at a low enough excitation power to avoid power broadening.

It is an aim of the present invention to provide a synthetic diamond material and a method of synthesising such material which comprises solid state spin defect photon emitters with an intrinsic inhomogeneous zero phonon line width approaching that of the transform limited value and which is stable with minimal spectral diffusion. The intrinsic inhomogeneous zero phonon line width is measured and calculated to include intrinsic line broadening effects such as intrinsic spectral drift but to exclude extrinsic effects such as temperature induced phonon broadening, excitation induced power broadening, photonic cavity broadening, and Stark tuned narrowing of the inhomogeneous zero phonon line width of solid state spin defects. Such narrow line width, stable solid state photon emitters constitute a major step forward towards solid state quantum computing and are also useful in other quantum optics, quantum sensing, and quantum processing applications.

SUMMARY OF INVENTION

According to a first aspect of the present invention there is provided a synthetic diamond material comprising one or more spin defects having a full width half maximum intrinsic inhomogeneous zero phonon line width of no more than 100 MHz.

According to a second aspect of the present invention there is provided a photonic device structure fabricated from synthetic diamond material, said photonic device structure comprising a photonic device layer including one or more photonic structures, each photonic structure comprising at least one spin defect disposed therein, wherein said at least one spin defect has a full width half maximum intrinsic inhomogeneous zero phonon line width of no more than 3.5 GHz and/or a single scan line width of no more than 100 MHz.

According to a third aspect of the present invention there is provided a method of fabricating a synthetic diamond material according to the first aspect of the invention or a photonic device structure according to the second aspect of the invention, the method comprising:
  selecting a synthetic diamond material comprising a single substitutional nitrogen concentration of no more than 100 ppb, 80 ppb, 60 ppb, 40 ppb, 20 ppb, 10 ppb, 5 ppb, or 1 ppb; and
  annealing the synthetic diamond material using a multi-stage annealing process comprising:
  a first annealing step at a temperature in a range 350 to 450° C. for at least 2 hours;
  a second annealing step at a temperature in a range 750 to 900° C. for at least 2 hours; and
  a third annealing step at a temperature in a range 1150° C. to 1550° C. for at least 2 hours.

According to a fourth aspect of the present invention there is provided a diamond-based quantum system comprising:
  a synthetic diamond material according to the first aspect of the invention or a photonic device structure according to the second aspect of the invention;
  an excitation arrangement configured to optically excite one or more spin defects in the synthetic diamond material or the photonic device structure; and
  a detector arrangement configured to detect photon emission from the one or more spin defects.

BRIEF DESCRIPTION OF THE DRAWINGS

For a better understanding of the present invention and to show how the same may be carried into effect, embodiments of the present invention will now be described by way of example only with reference to the accompanying drawings, in which.

DETAILED DESCRIPTION OF EMBODIMENTS OF THE INVENTION

Embodiments of the present invention provide a route for synthesising solid state emitters with a zero phonon line width approaching that of the transform limited value and which is stable over time with minimal spectral diffusion. As indicated in the summary of invention section, a synthetic diamond material has been fabricated comprising spin defects having a full width half maximum intrinsic inhomogeneous zero phonon line width of less than 100 MHz. This has been achieved by a combination of: (i) selection of a suitable synthetic diamond material; and (ii) treatment of the selected synthetic diamond material using a multistage annealing technique.

The synthetic diamond material utilized as the staring material for fabricating the aforementioned is preferably a CVD synthetic diamond material and particularly a high purity, low strain CVD synthetic diamond material such as is described in WO01/096633, WO2010/010344, and WO2010/010352. These materials have a single substitutional nitrogen concentration of no more than 100 ppb, 80 ppb, 60 ppb, 40 ppb, 20 ppb, 10 ppb, 5 ppb, or 1 ppb. Such materials provide a reasonably low strain, uniform electronic environment in which the spin defects can be disposed.

For example, WO01/096633 describes a method for synthesising very high purity single crystal CVD diamond material which has one or more of the following electronic and/or optical characteristics which are indicative of its high purity and crystallographic quality:
(i) a $\mu\tau$ product measured at 300 K greater than $1.5 \times 10^{-6}$ cm$^2$V$^{-1}$ where $\mu$ is the mobility and $\tau$ is the lifetime of the charge carriers;
(ii) an electron mobility ($\mu_e$) measured at 300K greater than 2400 cm$^2$V$^{-1}$s$^{-1}$;
(iii) a hole mobility ($\mu_h$) measured at 300K greater than 2100 cm$^2$V$^{-1}$s$^{-1}$;
(iv) a collection distance greater than 150 µm measured at an applied field of 1 V/µm and 300 K;
(v) a photoluminescence (PL) line related to the cathodoluminescence (CL) line at 575 nm, measured at 77 K under 514 nm Ar ion laser excitation (nominally 300 mW incident beam), which has a peak height<$\frac{1}{25}$ of the diamond Raman peak at 1332 cm$^{-1}$;
(vi) a strong free exciton (FE) emission, wherein the strength of the free exciton emission excited by 193 nm ArF excimer laser at room temperature is such that the quantum yield for free exciton emission is at least 10$^{-5}$; and
(vii) in electronic paramagnetic resonance (EPR), a spin density<$1 \times 10^{17}$ cm$^{-3}$ at g=2.0028.

Such single crystal CVD diamond material preferably has one or more of the following impurity characteristics:
(i) a level of any single impurity of not greater than 1 ppm and a total impurity content of not greater than 5 ppm where impurity excludes hydrogen and its isotopic forms; and
(ii) in electron paramagnetic resonance (EPR), a single substitutional nitrogen centre $N_s^0$ at a concentration <100 ppb;

The aforementioned material is sometimes referred to as electronic grade single crystal CVD diamond material. Further improvements to the material's chemical and isotopic purity are described in WO2010/010344, and WO2010/010352 leading to material which is sometimes referred to as quantum grade single crystal CVD diamond material. Such material may be characterized by one or more of the following characteristics in addition to those of the electronic grade material described above:
(i) a spin defect decoherence time $T_2$ at room temperature of 300 µs or more, preferably 500 µs or more, and more preferably 1 ms or more; and
(ii) an intrinsic inhomogeneous spin defect zero phonon line width of 500 MHz or less, 300 MHz or less, 200 MHz or less, 150 MHz or less, 100 MHz or less, 80 MHz or less, and most preferably 50 MHz or less.

Such single crystal CVD diamond material may have one or more of the following impurity characteristics:
(i) a total nitrogen concentration of 20 ppb or less, 10 ppb or less, or 5 ppb or less;
(ii) a concentration of NV centres of 10 ppb or less;
(iii) a total concentration of $^{13}$C of 0.9% or less;
(iv) a concentration of boron (and/or a concentration of uncompensated substitutional boron) of 100 ppb or less, 50 ppb or less, 20 ppb or less, 10 ppb or less, 5 ppb or less, 2 ppb or less, 1 ppb or less, 0.5 ppb or less, 0.2 ppb or less, or 0.1 ppb or less;
(v) a concentration of silicon of 100 ppb or less, 50 ppb or less, 20 ppb or less, 10 ppb or less, 5 ppb or less, 2 ppb or less, 1 ppb or less, 0.5 ppb or less, 0.2 ppb or less, 0.1 ppb or less, or 0.05 ppb or less;
(vi) a concentration of the silicon-vacancy (referred to as "SiV"), characterised by the intensity of the 737 nm photoluminescence (PL) line normalised against the intensity of the diamond Raman line at a shift of about 1332.5 cm$^{-1}$, both measured at a temperature of about 77 K, of 0.5 ppb or less, 0.2 ppb or less, 0.1 ppb or less, 0.05 ppb or less, 0.02 ppb or less, 0.01 ppb or less, or 0.005 ppb or less;
(vii) a concentration of intrinsic paramagnetic defects (i.e. defects which have a non-zero magnetic spin) of 1 ppm or less, 0.5 ppm or less, 0.2 ppm or less, 0.1 ppm or less, 0.05 ppm or less, 0.02 ppm or less, 0.01 ppm or less, 0.005 ppm or less, or 0.001 ppm or less;
(viii) a concentration of any single non-hydrogen impurity of 5 ppm or less, 1 ppm or less, or preferably 0.5 ppm or less;
(ix) a total impurity content excluding hydrogen and its isotopes of 10 ppm or less, 5 ppm or less, 2 ppm or less; and
(x) a concentration of hydrogen impurities (specifically hydrogen and its isotopes) of $10^{18}$ cm$^{-3}$ or less, $10^{17}$ cm$^{-3}$ or less, $10^{16}$ cm$^{-3}$ or less, or $10^{15}$ cm$^{-3}$ or less.

The single crystal CVD diamond material may have one or more of the aforementioned impurity characteristics throughout a majority volume of 50%, 60%, 70%, 80%, 90%, 95%, or throughout the entire volume of the single crystal CVD diamond material. Alternatively, the single crystal CVD diamond material may comprise a plurality of layers having different quantities and/or distributions of impurities. In this case, one or more of the layers may have one or more of the aforementioned impurity characteristics.

Despite the progress in fabricating single crystal CVD synthetic diamond material with high crystallographic quality and chemical and isotopic purity, such diamond materials still include a variety of crystal defects which can interact with electronic/spin defects in order to detrimentally affect the zero phonon emission line width and spectral stability of the spin defects. Some examples of point defects in synthetic diamond material include: silicon containing defects such as silicon-vacancy defects (Si—V), silicon di-vacancy defects (Si—V$_2$), silicon-vacancy-hydrogen defects (Si—V:H), silicon di-vacancy hydrogen defects (S—V$_2$:H); nickel containing defects; chromium containing defects; and nitrogen containing defects such as single substitutional nitrogen, multi-nitrogen defect structures, and nitrogen-vacancy structures such as nitrogen-vacancy defects (N—V), di-nitrogen vacancy defects (N—V—N), and nitrogen-vacancy-hydrogen defects (N—V—H). These defects are typically found in a neutral charge state or in a negative charge state. Isolated vacancy defects, di-vacancies, and larger vacancy clusters are also typically found in synthetic diamond materials. As such, it will be appreciated that there is a rich variety of defects within synthetic diamond material.

The negatively charged nitrogen-vacancy defect (NV⁻) in synthetic diamond material has attracted a lot of interest as a useful quantum spin defect because it has several desirable features including:

(i) Its electron spin states can be coherently manipulated with high fidelity owing to an extremely long coherence time (which may be quantified and compared using the transverse relaxation time $T_2$);

(ii) Its electronic structure allows the defect to be optically pumped into its electronic ground state allowing such defects to be placed into a specific electronic spin state even at non-cryogenic temperatures. This can negate the requirement for expensive and bulky cryogenic cooling apparatus for certain applications where miniaturization is desired. Furthermore, the defect can function as a source of photons which all have the same spin state; and (iii) Its electronic structure comprises emissive and non-emissive electron spin states which allows the electron spin state of the defect to be read out through photons. This is convenient for reading out information from synthetic diamond material used in sensing applications such as magnetometry, spin resonance spectroscopy and imaging. Furthermore, it is a key ingredient towards using the NV⁻ defects as qubits for long-distance quantum communications and scalable quantum computation. Such results make the NV⁻ defect a competitive candidate for solid-state quantum information processing (QIP).

In light of the above, preferably the spin defects of the present invention correspond to NV⁻ spin defects. However, it is envisaged that the methodology described in the present specification could be applied to other spin defects.

In order to improve the emission line width and spectral stability of a selected spin defect it would be desirable to provide a solid state material which includes the selected spin defects while excluding all other defects which detrimentally affect the spin and emission characteristics of the selected spin defect. As previously indicated, a high purity, low strain CVD synthetic diamond material is considered to provide a useful starting point for the provision of a low interference crystal matrix in which the spin defects of interest may be disposed. However, while such materials as described in WO01/096633, WO2010/010344, and WO2010/010352 provide a reasonably low strain, uniform electronic environment in which the spin defects can be disposed, the material still includes a variety of crystal defects which can interact with the spin defects in order to detrimentally affect the emission line width and spectral stability of the spin defects. For example, electronic grade CVD synthetic diamond material will comprise a residual quality of single substitutional nitrogen. While the residual concentration of single substitutional nitrogen is generally no more than 100 ppb within the diamond lattice such low concentrations of defects are still significant for quantum optics applications.

In light of the above, the present inventors have developed a multi-stage annealing process to systematically remove crystal defects which detrimentally affect the emission line width and spectral stability of spin defects, such as the NV⁻ spin defect, thereby improving the emission line width and spectral stability of spin defects within a high purity diamond matrix.

The method comprises: selecting a synthetic diamond material comprising a single substitutional nitrogen concentration of no more than 100 ppb (optionally 80 ppb, 60 ppb, 40 ppb, 20 ppb, 10 ppb, 5 ppb, or 1 ppb); and performing a multi-stage annealing process including a first annealing step at a temperature in a range 350 to 450° C. for at least 2 hours (optionally at least 4, 6, or 8 hours), a second annealing step at a temperature in a range 750 to 900° C. for at least 2 hours (optionally at least 4, 6, or 8 hours), and a third annealing step at a temperature in a range 1150° C. to 1550° C. for at least 2 hours (optionally at least 4, 6, or 8 hours). Such a multi-stage annealing process has been found to significantly improve the emission line width and spectral stability of spin defects within a diamond matrix which is already of high purity and relatively low strain. While not being bound by theory, the reasoning behind why this multi-stage annealing process is successful in achieving stable and near transform limited line width spin defects is as follows.

Annealing diamond material changes the nature and distribution of defects within the diamond lattice. For example, multi-atom defects can be split, defects can become mobile and move through the diamond lattice, and defects can combine to form new defect types. The temperature at which these different processes occur varies and will also be dependent on the type of impurities within the diamond lattice. In high purity CVD synthetic diamond materials the defect structure is dominated by nitrogen containing defects and vacancy containing defects. Nitrogen is predominantly in the form of isolated nitrogen atoms which may be located on lattice sites or in interstitial locations. Vacancies are present in isolated form, as di-vacancies, and as larger vacancy clusters.

The first annealing step at a temperature in a range 350 to 450° C. for at least 2 hours (optionally at least 4, 6, or 8 hours) is intended to move interstitial nitrogen atoms from interstitial sites to lattice sites. This requires interstitial nitrogen atoms to combine with vacancy defects present on lattice sites such that the vacancy is replaced with a nitrogen atom on the lattice site. It is believed that an annealing temperature of around 400° C. is optimal for achieving this process for eliminating interstitial nitrogen defects compared with a process in which interstitial nitrogen defects combine to form interstitial-interstitial di-nitrogen defects which may dominate at higher annealing temperatures. That is, at temperatures around 400° C. it is believed that the main loss mechanism for interstitial nitrogen atoms is to combine with vacancies on lattice sites rather than forming more stable di-nitrogen interstitial defects. While 2 hours is believed to be sufficient time to remove or significantly reduce interstitial nitrogen atom at a temperature around 400° C., a longer annealing time of at least 4, 6, or 8 hours may be desirable to ensure that this is the case.

Once interstitial nitrogen atoms have been removed (or at least reduced) by the aforementioned annealing step, a second annealing step at a temperature in a range 750 to 900° C. is performed for at least 2 hours (optionally at least 4, 6, or 8 hours). This step is intended to cause the formation of NV defects by migrating vacancies to combine with nitrogen atoms located on lattice sites. At temperatures much less than 800° C. it is believed that the vacancies are not sufficiently mobile to form NV defects in a reasonable time frame. At temperatures significantly above 800° C. it is believed that the greater thermal energy in the diamond lattice means the strain field around the isolated nitrogen defects is no longer sufficient to lead to it being the dominant loss mechanism for vacancies migrating through the diamond lattice. For example, at 1200° C. very few NV defects are formed while at temperatures significantly above 1400° C. the nitrogen atoms located on lattice sites become mobile in the presence of vacancy defects which is also undesirable. While 2 hours is believed to be sufficient time to convert a significant number of vacancies into NV defects via a migration and capture mechanism at a temperature around 800° C., there is some evidence to suggest that a significant concentration of vacancy defects remains after annealing for 2 hours. Accordingly, a longer annealing time of at least 3 hours, 4 hours, 5 hours, 6 hours, 8 hours, or 10 hours at a temperature around 800° C. may be desirable to ensure that a significant concentration of residual vacancy defects does not remain present within the diamond lattice.

Finally, it is believed that in addition to the formation of NV defects at 800° C., the other main loss mechanism for isolated vacancies at this temperature is to form di-vacancy defects. Di-vacancy defects anneal out at temperatures above 1150° C. and thus a third annealing step is performed at a temperature above 1150° C. for at least 2 hours (optionally at least 4, 6, or 8 hours), in order to remove di-vacancy defects. In addition, it is believed that intrinsic $sp^2$ carbon type defects and hydrogen begin to migrate or anneal out at around 1200° C. Accordingly, it may be advantageous to perform the third annealing step at a higher temperature of at least 1200° C., 1300° C., or 1350° C. As previously indicated, at temperatures significantly above 1400° C. it is believed that nitrogen atoms located on lattice sites become mobile in the presence of vacancy defects and thus it is considered that it may be advantageous to ensure that the third annealing step does not significantly exceed 1400° C. although it can be possible to use a temperature up to 1550° C. if the second annealing step is performed for a sufficiently long time period such that there are very few vacancies thus making nitrogen atoms less mobile. As such, the third annealing step may be performed at a temperature of at least 1200° C., 1300° C., or 1350° C. and/or a temperature of no more than 1500° C., 1450° C., or 1400° C. While 2 hours is believed to be sufficient time to remove or significantly reduce di-vacancies, hydrogen and intrinsic $sp^2$ carbon defects, a longer annealing time of at least 3 hours, 4 hours, 6 hours, or 8 hours may be desirable to ensure that a significant concentration of residual di-vacancy defects, hydrogen, and $sp^2$ carbon defects does not remain present within the diamond lattice.

In relation to the above, it should be noted that high annealing temperatures can lead to graphitisation of the diamond material. Accordingly, high temperature annealing steps may be performed under an inert atmosphere and/or under diamond stabilizing pressure to prevent graphitisation. Furthermore, after performing the multi-stage annealing process the synthetic diamond material is advantageously acid cleaned and then annealed in oxygen to remove any residual graphite.

Preferably the synthetic diamond material is CVD synthetic diamond material. Furthermore, preferably the one or more spin defects are NV⁻ spin defects. While the aforementioned multi-stage annealing process is described in relation to the formation of NV spin defects in place of interstitial nitrogen defects and various forms of vacancy defect, such a multi-stage annealing process can also be used to effectively "clean-up" the diamond lattice to provide a more stable electronic environment for other spin defects.

It has also been noted that suitable synthetic diamond starting materials may comprise a surface layer which is damaged and highly strained due to mechanical polishing. In this case, a surface layer may be removed by, for example, etching prior to application of the multistage annealing process. For example, a surface layer of the synthetic diamond material may be removed by applying an Ar/Cl₂ etch followed by an O₂ etch to yield a low damage, low strain surface prior to application of the multistage annealing process.

Utilizing the above described multi-stage annealing procedure a synthetic diamond material has been fabricated comprising spin defects with a full width half maximum intrinsic inhomogeneous zero phonon line width of no more than 100 MHz. In fact, it has been found that the multi-stage annealing procedure is capable of achieving a full width half maximum intrinsic inhomogeneous zero phonon line width of no more than 80 MHz, 60 MHz, 50 MHz, or 40 MHz. The full width half maximum intrinsic inhomogeneous zero phonon line width may be averaged over at least 10, 20, 30, 50, 75, 100, 500, or 1000 seconds. Furthermore, the full width half maximum intrinsic inhomogeneous zero phonon line width may be averaged over at least 10, 20, 30, 50, 75, 100, 500, or 1000 spectral scans. Further still, the multi-stage annealing process can produce a material comprising spin defects with improved emission characteristics near an external surface of the synthetic diamond material. This is advantageous for optically addressing spin defects, outcoupling photons from spin defects, and providing optical outcoupling structures including photonic cavities coupled to the spin defects. For example, the one or more spin defects may be located no more than 1 μm, 500 nm, 200 nm, 100 nm, 50 nm, 30 nm, 10 nm, or 5 nm from a surface of the synthetic diamond material.

Furthermore, the multi-stage annealing process is intended to provide a significant number of spin defects which are provided in a stable, low strain environment within the crystal lattice. For many applications it is advantageous for the synthetic diamond material to comprise a plurality of spin defects each having a stable spectral line width of less than 100 MHz, 80 MHz, 60 MHz, 50 MHz, or 40 MHz and most preferably a majority (e.g., at least 50%, 60%, 70%, 80%, or 90%) of the spin defects distributed through the synthetic diamond material will meet this criterion.

In certain embodiments of the present invention the spin defects are formed during growth of the synthetic diamond material where a nitrogen atom and a vacancy are incorporated into the crystal lattice as a nitrogen-vacancy pair during growth. The spin defects can also be formed after material synthesis using defects incorporated during the material growth process. For example, NV defects can be formed from separate nitrogen and vacancy defects incorporated during the growth process by subsequent annealing the material using the multi-stage annealing process as previously described.

In the above cases, the spin defects can be distributed throughout the synthetic diamond material. Alternatively, a thin layer of doped material may be grown on or within an intrinsic crystal structure such that the spin defects are located only in a thin layer of the synthetic diamond material, e.g. a so-called delta-layer having nano-scale depth. Alternatively still, it is also known to implant nitrogen into an as-grown diamond material to form a layer of nitrogen with subsequent annealing at around 800° C. to form NV defects. For example, Rabeau et al. and Santori et al. have discussed the dynamics of nitrogen implantation and annealing [see Appl. Phys. Lett. 88, 023113 (2006) and Phys. Rev. B 79, 125313 (2009)]. It has also been found that NV defects formed by such implantation methods can have a stable spectral line width of less than 100 MHz, 80 MHz, 60 MHz, 50 MHz, or 40 MHz if a multi-stage annealing process as described herein is utilized after the implantation step. In this case, the spin defects will be located in a thin layer within the synthetic diamond material, e.g. a 2-D spin defect array. For example, stable spectral line width of less than 100 MHz, 80 MHz, 60 MHz, 50 MHz, or 40 MHz have been observed in single crystal CVD diamond samples which have been implanted with nitrogen atoms at an energy of about 85 keV to a nominal depth of about 100 nm and to a nitrogen concentration of about $10^9$ $cm^{-2}$ to $10^{10}$ $cm^{-2}$ followed by a multi-stage annealing process as described herein.

In light of the above, the synthetic diamond material may comprise a layer of spin defects, said layer comprising at least $10^5$ $cm^{-2}$ spin defects and having a thickness no more than 1 μm, wherein the spin defects in said layer have a full width half maximum intrinsic inhomogeneous zero phonon line width of no more than 100 MHz, 80 MHz, 60 MHz, 50 MHz, or 40 MHz. The thickness of said layer is no more than 500 nm, 200 nm, 100 nm, 50 nm, 30 nm, 10 nm or 5 nm. Furthermore, the layer may comprise $10^5$ spin defects/$cm^2$ to $10^{11}$ spin defects/$cm^2$. The concentration of spin defects may be at least $10^6$ spin defects/$cm^2$, $10^7$ spin defects/$cm^2$, or $10^8$ spin defects/$cm^2$ and/or no more than $10^{10}$ spin defects/$cm^2$, $10^9$ spin defects/$cm^2$, or $10^8$ spin defects/$cm^2$, or any combination of these lower and upper limits depending on the desired spin defect concentration for a particular application. For example, the concentration of spin defects may be in a range $10^5$ spin defects/$cm^2$ to $10^{11}$ spin defects/$cm^2$, $10^5$ spin defects/$cm^2$ to $10^{10}$ spin defects/$cm^2$, $10^5$ spin defects/$cm^2$ to $10^9$ spin defects/$cm^2$, or $10^5$ spin defects/$cm^2$ to $10^8$ spin defects/$cm^2$. Thin diamond layers comprising a plurality of spin defects are useful for fabricating device layers and structures. Spin defect line widths reported for such thin layers of spin defects have been significantly worse that for bulk materials and/or isolated spin defects. However, spin defects within such layers having a low full width half maximum intrinsic inhomogeneous zero phonon line width can be achieved using the multi-stage annealing procedure described herein. Furthermore, the layer may be located no more than 1 μm, 500 nm, 200 nm, 100 nm, 50 nm, 30 nm, 10 nm or 5 nm from a surface of the synthetic diamond component.

Figure 1:
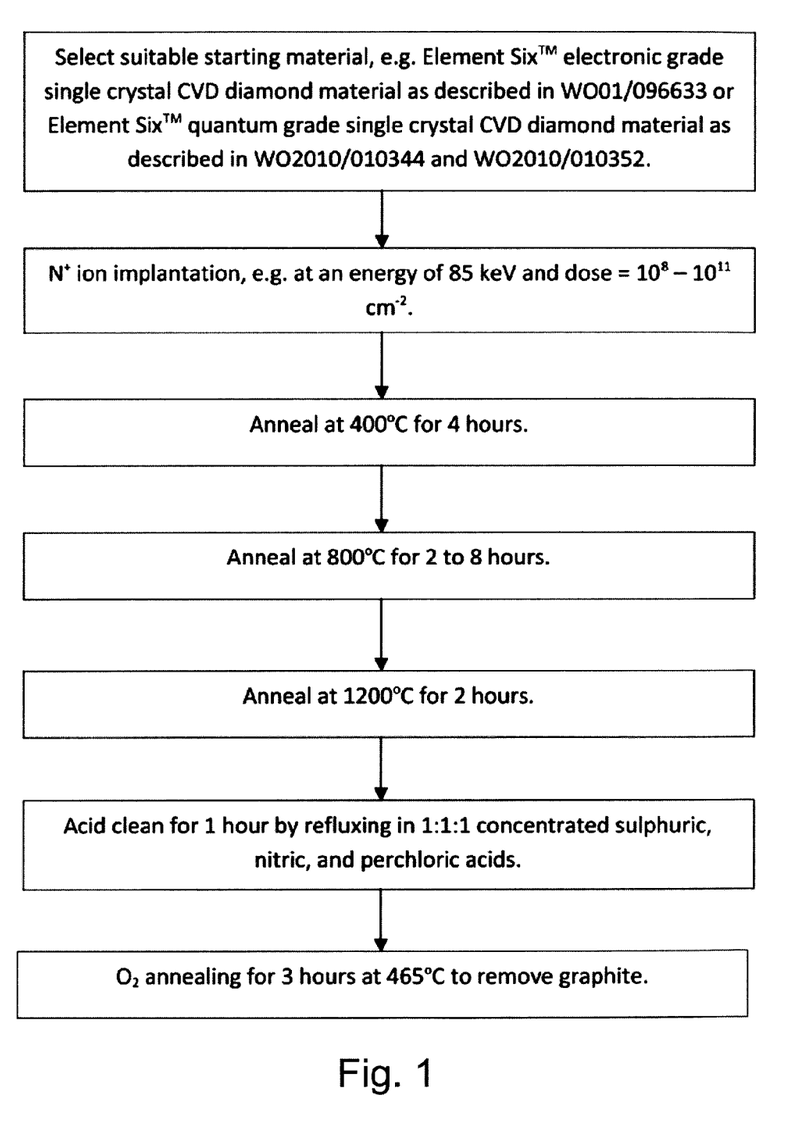
FIG. 1 shows a flow diagram illustrating an example of a method for fabricating a thin layer of spin defects located within a synthetic diamond component.

An example of a process for fabricating a thin layer of spin defects having narrow line width emission is illustrated in FIG. 1 which shows a flow diagram of the individual steps. The process comprises:

(1) Selecting a suitable starting material, e.g. Element Six™ electronic grade single crystal CVD diamond material as described in WO01/096633 or Element Six™ quantum grade single crystal CVD diamond material as described in WO2010/010344 and WO2010/010352.
(2) $N^+$ ion implantation, e.g. at an energy of 85 keV and dose=$10^8$-$10^{11}$ $cm^{-2}$.
(3) Annealing at 400° C. for 4 hours.
(4) Annealing at 800° C. for 2 to 8 hours.
(5) Annealing at 1200° C. for 2 hours.
(6) Acid cleaning for 1 hour by refluxing in 1:1:1 concentrated sulphuric, nitric, and perchloric acids.
(7) $O_2$ annealing for 3 hours at 465° C. to remove graphite.

Optionally a surface layer of the starting material is removed prior to $N^+$ ion implantation by applying an Ar/$Cl_2$ etch followed by an $O_2$ etch to yield a low damage, low strain surface.

Figure 2A:
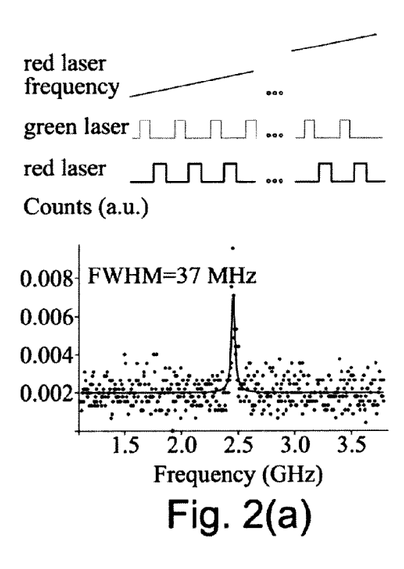
FIGS. 2(a) and 2(b) show spectral data for a thin layer of spin defects located within a synthetic diamond component.
Figure 2B:
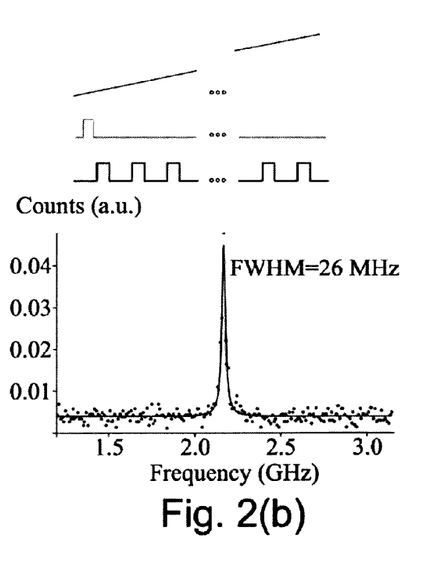

Spectral data for a thin layer of $NV^-$ defects fabricated using the aforementioned procedure is given in FIG. 2. The spectral data illustrates the spectral properties of the implanted and annealed $NV^-$ spin defects at low temperature with FIG. 2(a) illustrating the full width half maximum intrinsic inhomogeneous zero phonon line width and FIG. 2(b) illustrating the line width after correcting for spectral diffusion. Having regard to FIG. 2(a), the spectrum was taken by excitation with a scanning diode laser at 637.2 nm and collecting photons from $NV^-$ spin defects in the phonon side band. In every repetition of the pulse sequence, green re-pump light was applied for 1 ms, followed by 10 ms of red light. Fluorescence was collected only when the red laser was on. This pulse sequence was repeated as the red laser frequency was scanned. The scan was repeated thirty times and the data averaged during analysis.

Such an experiment gives the $NV^-$ spin defect line width with spectral diffusion under green illumination. Having regard to FIG. 2(b), the spectrum was taken under the same conditions as FIG. 2(a) except green light was only applied at the beginning of each laser scan. In addition, before averaging, the peak position for each individual scan was determined, and the scans were shifted so that the peak positions all line up. This analysis gives an indication of the line width without spectral diffusion caused by the green laser, and includes only the lifetime limited line width (FWHM=13 MHz) and any residual spectral diffusion caused by the red laser.

In relation to the above, instead of using 532 nm green light to re-pump the $NV^0$ state into $NV^-$, it is also possible to use a 757 nm laser re-pump which can convert NV centers back to the negatively charged state even at very low powers. This re-pump method reduces spectral diffusion due to lower intensity and energy per photon of the 575 nm excitation compared to more conventional 532 nm excitation.

It is also known that irradiating diamond material, for example with electrons, can form vacancy defects and that a subsequent annealing step at 800° C. can be used to form NV defects from the vacancy defects introduced by irradiation. Accordingly, it is envisaged that an electron irradiation step may also be performed prior to the multi-stage annealing process. Such an irradiation step may also be used in combination with an implantation technique.

In addition to the above, it is also envisaged that irradiation may be used in combination with the multi-stage annealing process to further reduce the concentration of defects within the diamond lattice which adversely affect the emission characteristics of the spin defects of interest. For example, formation of negatively charged NV defects for quantum optics application from neutral NV defects requires an electron donor within the diamond lattice. Typically, the electron donor will be a single substitutional nitrogen atom. As such, while the presence of single substitutional nitrogen may adversely affect the magnetic and optical properties of $NV^-$ spin defects, a certain level of single substitutional nitrogen may be required to function as electron donors to form $NV^-$ defects from neutral NV defects. This will result in a material comprising $NV^-$ defects and a corresponding concentration of $N^+$ defects for charge neutrality. However, it is believed that typically there will be a residual quantity of unconverted neutral single substitutional nitrogen which is a spin one-half defect and is detrimental to the spin properties of the $NV^-$ defect. It is believed that if a controlled concentration of vacancy defects is introduced by irradiation followed by a subsequent annealing step at 1200° C. then the residual nitrogen and vacancy defects can combine to form, for example, a spin zero defect N—V—N and hence the properties of the NV⁻ defects can be improved.

It should be noted that individual annealing steps as described herein may be known in the art. For example, B. Naydenov et al. have suggested an implantation and annealing technique at a temperature of 800° C. for fabricating NV⁻ spin defects. B. Naydenov et al. have also suggested that annealing at higher temperatures above 1000° C., 1100° C., or 1200° C. may be advantageous for removing various paramagnetic defects to increase the decoherence time of NV spin defects. Furthermore, Fu et al. [Appl. Phys. Lett. 96, 121907 (2010)] have suggested that annealing NV containing diamond material at 465° C. in an oxygen atmosphere can oxidize NV⁰ to NV⁻ near the surface of the sample. However, the present inventors are not aware of any disclosure of a three stage annealing process as described herein or any disclosure that such a multi-stage annealing process can result in stable, narrow zero phonon line width emission for spin defects as is required for quantum optics applications which require multi-photon entanglement. Indeed, it is possible that the oxidizing anneal described by Fu at al. could be performed after the multi-stage annealing process as described herein to convert near surface NV⁰ defects into NV⁻.

The intrinsic inhomogeneous zero phonon line emission of the annealed synthetic diamond product material is measured at a temperature below the Debye temperature, e.g. at a temperature below 10 Kelvin. Emission measurements can be taken while alternatively pumping with green and red laser light and scanning the zero phonon line emission. Intrinsic inhomogeneous zero phonon line widths of less than 100 MHz are obtained. Furthermore, the zero phonon line emission has been found to be stable over averaging times of at least 1 s, 10 s, 20 s, 50 s, and up to 100 s. Furthermore, the zero phonon line emission is stable even under green laser excitation and although re-pumps are required in bulk diamond samples no spectral diffusion is observed as a result of these re-pumps. Further still, there is no evidence to suggest that spectral diffusion will occur at more extended time periods.

The synthetic diamond material of certain embodiments of the present invention may comprise one or more of the electronic, optical, and impurity characteristics of the materials of WO01/096633, WO2010/010344, and WO2010/010352 as described earlier in this specification. Preferably, the synthetic diamond material comprises a single substitutional nitrogen concentration of no more than 100 ppb, 80 ppb, 60 ppb, 40 ppb, 20 ppb, 10 ppb, 5 ppb, or 1 ppb.

In addition, after the multi-stage annealing process as described herein the concentration of NV defects will be increased relative to the concentration of other spin defects within the diamond material which otherwise adversely affect the emission characteristics of the NV defects. As such, in addition to the characteristics of the pre-annealed material, the multi-stage annealing process leads to spin defects which have a narrower intrinsic inhomogeneous zero phonon line width. Furthermore, the multi-stage annealing process can produce a material comprising spin defects which have an improved decoherence time $T_2$ or a comparable decoherence time from a less pure starting material. For example, one or more spin defects within the material may have a decoherence time $T_2$ at room temperature of at least 100 μs, 300 μs, 500 μs, 1 ms, 2 ms, 5 ms, 10 ms, 50 ms, or 100 ms.

One or more photonic structures can be fabricated in the synthetic diamond material. The one or more spin defects can be located no more than 1 μm, 500 nm, 200 nm, 100 nm, 50 nm, 30 nm, 10 nm or 5 nm from the one or more photonic structures or within the one or more photonic structures. In this way a diamond device layer can be fabricated comprising one or more spin defects coupled to one or more photonic structures. Examples of suitable photonic structures include photonic beams and hybrid photonic crystals.

In addition to the above, the present inventors have also noted that while the fabrication of phonic device structures in synthetic diamond material has previously been reported, problems have arisen in providing spectrally stable spin defects within such photonic device structures. US2011-0309265 describes an etching procedure suitable for fabricating photonic structures in synthetic diamond material. It has been found that the multi-stage annealing procedure as described herein can be combined with the etching procedure as described in US2011-0309265 in order to fabricate photonic structures in synthetic diamond material comprising spin defects which are reasonably spectrally stable and have a relatively narrow line width. The multi-stage annealing procedure as described herein may be applied either before or after the etching procedure as described in US2011-0309265 in order to stabilize the spectrally properties of spin defects located within photonic structures.

In light of the above, according to another aspect of the invention there is provided a photonic device structure fabricated from synthetic diamond material, said photonic device structure comprising a photonic device layer including one or more photonic structures, the or each photonic structure comprising at least one spin defect disposed therein, wherein said at least one spin defect has a full width half maximum intrinsic inhomogeneous zero phonon line width of no more than 3.5 GHz, 3.0 GHz, or 2.6 GHz and/or a single scan line width of no more than 100 MHz. The photonic device layer can be fabricated from the synthetic diamond material according to the first aspect of the invention.

Figure 3A:
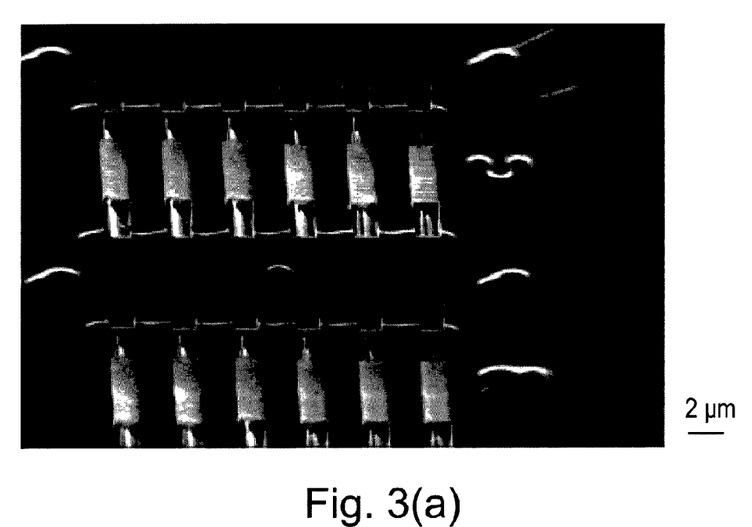
FIGS. 3(a) and 3(b) illustrate scanning electron microscope (SEM) images of beams and hybrid photonic crystals fabricated in synthetic diamond material.
Figure 3B:
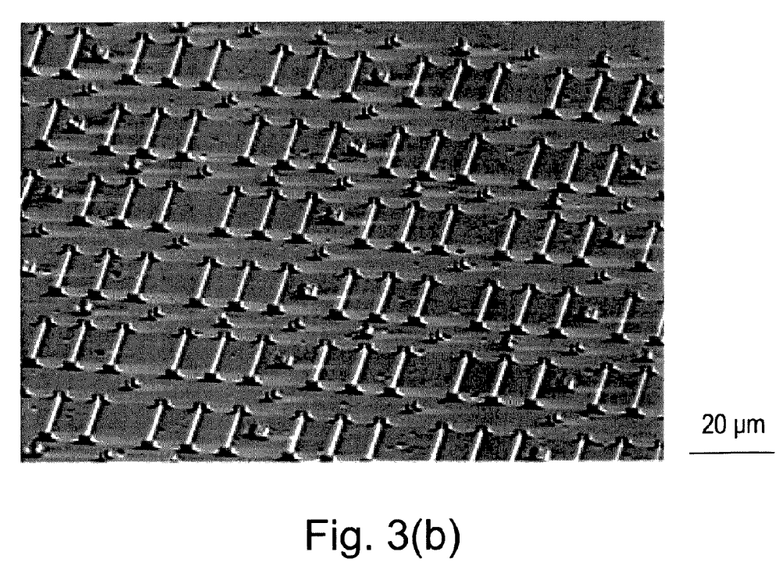

FIGS. 3(a) and (b) illustrate scanning electron microscope (SEM) images of beams and hybrid photonic crystals comprising spin defects as fabricated using the methodology described herein. These images illustrate examples of single device layers of photonic diamond structures comprising NV⁻ spin defects.

Figure 4:
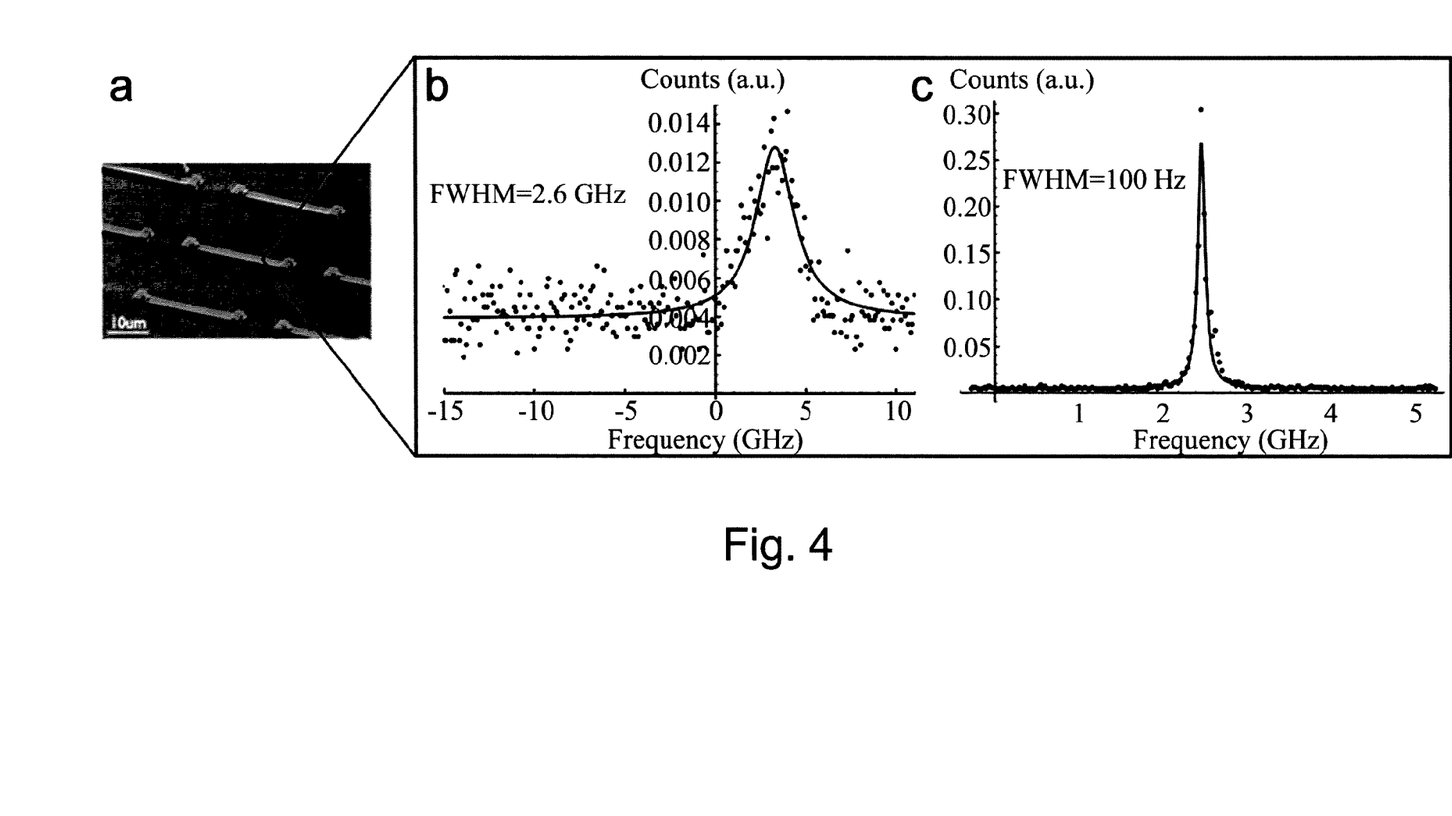
FIGS. 4(a) to 4(c) show spectral data for a spin defect located within a photonic synthetic diamond structure.

Spectral data for a spin defect located within a photonic structure is given in FIG. 4 which shows the spectral properties of NV⁻ spin defects inside nanoscale optical devices fabricated using the multi-stage annealing technique as described herein in combination with a suitable etching technique as described, for example, in US2011-0309265. FIG. 4(a) shows an SEM image of suspended diamond waveguides fabricated on top of a bulk diamond substrate. The waveguides have a length of approximately 20 μm and width of approximately 200 nm. FIG. 4(b) shows spectral data for an NV⁻ spin defect located inside a suspended waveguide. The data was taken in the same way as described previously for FIG. 2(a) and the line width includes the effects of spectral diffusion. FIG. 4(c) shows spectral data for an NV⁻ spin defect located inside a suspended waveguide where the data was taken in the same way as described previously for FIG. 2(b) and the line width excludes the effects of spectral diffusion.

The material as described herein has been engineered for use in diamond-based quantum systems and devices. Accordingly, another aspect of the present invention provides a diamond based quantum system comprising the material and/or photonic device structures as described herein. Such a system will also comprise an excitation arrangement configured to optically excite the one or more spin defects in the synthetic diamond material and a detector arrangement configured to detect photon emission from the one or more spin defects in the synthetic diamond material. An example of such a multi-photon interference system is described in the background section. Such a system requires at least two spin defects and the excitation arrangement is configured to individually address the at least two spin defects. The system further comprises a photon interference arrangement configured to overlap photon emissions from the at least two spin defects. Furthermore, the detector arrangement is configured to detect photon emissions from the at least two spin defects after passing through the photon interference arrangement, wherein the detector arrangement is configured to resolve sufficiently small differences in photon detection times that photon emissions from the at least two synthetic solid state emitters are quantum mechanically indistinguishable resulting in quantum entanglement between indistinguishable photon emissions from different spin defects.

The system as described above is similar in configuration to that recently proposed and discussed in the background section. However, because of the improved spin defect emission line width and spectral stability it is considered that Stark tuning is not an essential requirement and the device may be simplified so as to not require tuning components. That said, it is also envisaged that the material of the present invention can be used in combination with Stark tuning to achieve a combined technical effect. Filtering may also be utilized although the high quality emission characteristics will mean that less photons will need to be discarded leading to higher data acquisition rates. Further still, because the frequency of the photon emission is more precisely defined using the material of the present invention then the detector arrangement does not require such high resolution to photon detection times to ensure that photon emissions from the at least two synthetic solid state emitters are quantum mechanically indistinguishable resulting in quantum interference between indistinguishable photon emissions from different synthetic solid state photon emitters. Again, this will result in higher data acquisition rates.

In addition to the above, it should also be noted that the synthetic diamond material as described herein may be suitable for other applications beyond quantum sensing and processing including radiation detectors, optical, and electronic applications.

While this invention has been particularly shown and described with reference to preferred embodiments, it will be understood to those skilled in the art that various changes in form and detail may be made without departing from the scope of the invention as defined by the appendant claims.

The invention claimed is:

1. A synthetic diamond material comprising one or more spin defects having a full width half maximum intrinsic inhomogeneous zero phonon line width of no more than 100 MHz,
wherein the full width half maximum intrinsic inhomogeneous zero phonon line width is averaged over one or both of: at least 10 seconds; and at least 10 spectral scans,
wherein the synthetic diamond material is chemical vapor deposited (CVD) synthetic diamond material, and
wherein the one or more spin defects are negatively charged nitrogen vacancy (NV$^-$) spin defects, and
wherein the one or more s in defects have a decoherence time $T_2$ at room temperature of at least 500 µs.

2. A synthetic diamond material according to claim 1, wherein the full width half maximum intrinsic inhomogeneous zero phonon line width is no more than 40 MHz.

3. A synthetic diamond material according to claim 1, wherein the full width half maximum intrinsic inhomogeneous zero phonon line width is averaged over at least 100 seconds.

4. A synthetic diamond material according to claim 1, wherein the full width half maximum intrinsic inhomogeneous zero phonon line width is averaged over at least 100 spectral scans.

5. A synthetic diamond material according to claim 1, wherein the synthetic diamond material comprises a layer of said spin defects, the layer comprising at least $10^5$ spin defects/cm$^2$ and having a thickness no more than 1 µm.

6. A synthetic diamond material according to claim 1, wherein at least 50% of the spin defects have a total spectral line width of less than 100 MHz.

7. A synthetic diamond material according to claim 1, further comprising one or more photonic structures fabricated in the synthetic diamond material.

8. A diamond-based quantum system comprising:
a synthetic diamond material according to claim 1;
an excitation arrangement configured to optically excite one or more spin defects in the synthetic diamond material; and
a detector arrangement configured to detect photon emission from the one or more spin defects.

9. A synthetic diamond material comprising one or more spin defects having a full width half maximum intrinsic inhomogeneous zero phonon line width of no more than 100 MHz,
wherein the full width half maximum intrinsic inhomogeneous zero phonon line width is averaged over one or both of: at least 10 seconds; and at least 10 spectral scans,
wherein the synthetic diamond material is chemical vapor deposited (CVD) synthetic diamond material, and
wherein the one or more spin defects are negatively charged nitrogen vacancy (NV$^-$) spin defects, and
wherein the one or more spin defects are located no more than 1 µm from a surface of the synthetic diamond material.

10. A synthetic diamond material according to claim 9, wherein said layer comprises $10^5$ spin defects/cm$^2$ to $10^{11}$ spin defects/cm$^2$.

11. A synthetic diamond material comprising one or more spin defects having a full width half maximum intrinsic inhomogeneous zero phonon line width of no more than 100 MHz,
wherein the full width half maximum intrinsic inhomogeneous zero phonon line width is averaged over one or both of: at least 10 seconds; and at least 10 spectral scans,
wherein the synthetic diamond material is chemical vapor deposited (CVD) synthetic diamond material, and
wherein the one or more spin defects are negatively charged nitrogen vacancy (NV$^-$) spin defects,
wherein the synthetic diamond material comprises a layer of said spin defects, the layer comprising at least $10^5$ spin defects/cm$^2$ and having a thickness no more than 1 µm, and
wherein the thickness of said layer is no more than 100 nm.

12. A synthetic diamond material comprising one or more spin defects having a full width half maximum intrinsic inhomogeneous zero phonon line width of no more than 100 MHz, and
- one or more photonic structures fabricated in the synthetic diamond material,
- wherein the full width half maximum intrinsic inhomogeneous zero phonon line width is averaged over one or both of: at least 10 seconds; and at least 10 spectral scans,
- wherein the synthetic diamond material is chemical vapor deposited (CVD) synthetic diamond material, and
- wherein the one or more spin defects are negatively charged nitrogen vacancy (NV) spin defects, and
- wherein the one or more spin defects are located no more than 1 μm from the one or more photonic structures or within the one or more photonic structures.

13. A method of fabricating a synthetic diamond material, the method comprising:
- selecting a synthetic diamond material comprising a single substitutional nitrogen concentration of no more than 100 ppb; and
- annealing the synthetic diamond material using a multi-stage annealing process comprising:
  - a first annealing step at a temperature in a range 350 to 450° C. for at least 2 hours;
  - a second annealing step at a temperature in a range 750 to 900° C. for at least 2 hours; and
  - a third annealing step at a temperature in a range 1150° C. to 1550° C. for at least 2 hours; said synthetic diamond comprising
- one or more spin defects having a full width half maximum intrinsic inhomogeneous zero phonon line width of no more than 100 MHz,
- wherein the full width half maximum intrinsic inhomogeneous zero phonon line width is averaged over one or both of: at least 10 seconds; and at least 10 spectral scans,
- wherein the synthetic diamond material is chemical vapor deposited (CVD) synthetic diamond material, and
- wherein the one or more spin defects are negatively charged nitrogen vacancy ($NV^-$) spin defects.

14. A method according to claim 13, further comprising implanting a layer of nitrogen into the synthetic diamond material prior to the multi-stage annealing process.

15. A method according to claim 13, further comprising irradiating the synthetic diamond material prior to the multi-stage annealing process to form vacancy defects.

* * * * *